United States Patent [19]

Moore

[11] Plant 4,717

[45] May 19, 1981

[54] CLIMBING MINIATURE ROSE PLANT

[76] Inventor: Ralph S. Moore, 2519 E. Noble Ave., Visalia, Calif. 93277

[21] Appl. No.: 111,842

[22] Filed: Jan. 14, 1980

[51] Int. Cl.[3] ..... A01H 5/00

[52] U.S. Cl. ..... Plt./6

[58] Field of Search ..... Plt./6

*Primary Examiner*—James R. Feyrer

[57] ABSTRACT

The subject of the present disclosure is a new and distinct variety of hybrid miniature rose plant characterized by the red color of buds and flowers and further identified by the climbing or "rambler" habit of growth.

2 Drawing Figures

The present invention relates to a new and distinct variety of hardy, climbing (ground cover) type rose plant of the miniature class; the variety being primarily characterized—as to novelty—by medium to dark red buds and flowers which in general color effect are similar to Magic Dragon, climbing miniature, not patented.

The variety is further characterized by:

The abundance of flowers borne in clusters of 3 to 5 or more and the repeat flowering habit.

Little or no fragrance.

A plant which is vigorous, of rambling growth and spreading shape with glossy small foliage with pointed leaflets; the buds and flowers being similar in form to Orange Triumph (polyantha—not patented), but smaller in size.

The plant, which has a normal height of 12–14 inches and a spread of 5 to 7 feet or more across, can easily be maintained at lesser size by occasional trimming.

A plant which grows and blooms satisfactorily outdoors; is good for growing in tubs or large pots; is especially good as a ground cover or low climber on a trellis or fence and make a very attractive specimen when budded high (5–6 feet) and grown as a "weeping" tree rose.

The present variety of miniature rose was originated by me at Sequoia Nursery located at Visalia, Calif., under conditions of careful control and observation, as a cross between Dortmund (climber—not patented) as the seed parent and Little Chief (miniature—not patented) as the pollen parent.

Subsequent to origination of the variety I successfully asexually reproduced it at Sequoia Nursery, located as aforesaid, by budding as well as by cuttings; the reproductions having run true in all respects.

The color photographs illustrate the variety (1) growing as a weeping tree (standard) (one year top budded at height of five feet), and (2) a close-up showing foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; vigorous, low spreading growth (rambler type); seedling; outdoors; garden decoration.

Class: Climbing miniature.

*Variety name.*—Firefall.

Flowers borne: Several together (3 to 5 or more) on slender, wirey, quite thorny, stems arising from canes of previous season's growth and on tips and laterals of current season's growth.

Quantity of bloom: Abundant outside.

Bud:

*Peduncle.*—Medium length; slender but sturdy; erect; medium to light green (bronzy on side of stem exposed to sun); hairs — some hairs.

*Before calyx breaks; size.*—Small. Form short; pointed with several short hairs and several small foliaceous appendages on surface of bud; with foliaceous parts extending beyond the tip of the bud equal to less than ½ of its length. Color — medium green to bronzy.

*As calyx breaks, color.*—Medium dark red. Opening: opens well in all weather.

Bloom:

*Size when fully open.*—Small, averaging about 40 mm (1½") or smaller.

*Petalage.*—Double — averaging up to 50 in early part of season and as few as 25–30 in fall, arranged regularly plus sometimes several petaloids.

*Form.*—Cupped at first, becoming more flat, and later at maturity open with petals remaining in similar shape and position. Open flowers may show stamens.

Petals: Fairly thick; satiny on inside and on outside surface.

*Shape.*—Outside petals, broad lanceolate with rounded tip; intermediate — broad lanceolate with rounded tip; inside — lanceolate with acute or rounded tip.

Color: Newly opened flower from a plant grown outdoors.

*Outside petal.*—Outside surface — near Chrysanthemum Crimson 824/2 with both lighter and darker areas becoming near white at base. Inside surface — near Chrysanthemum Crimson 824 with both lighter and darker areas and small near white area at base.

*Intermediate petal.*—Outside surface — similar to outside. Inside surface — similar to outside petal.

*Inner petal.*—Outside surface — same as intermediate petal; inside surface — same as intermediate petal. NOTE: Colors above observed on samples taken end of October; spring flowers may be slightly lighter red and of brighter hue. General color effect; newly opened flowers — color medium to dark red. Three days open — color similar to newly opened flowers. Behavior — opens well in all weather. Spent petals drop off. Flower longevity (May 1979) — plant in large pot 5–10 days or longer. Cut flowers at living room temperature 4–6 days.

Reproductive organs:

*Stamens.*—Few to several, arranged regularly about pistils.

*Filaments.*—Varying length, medium to short, yellow.

*Anthers.*—Usually well formed; yellow.

*Pollen.*—None.

*Pistils.*—Average number.

*Styles.*—Fairly even; short length; bunched; color — whitish.

*Ovaries.*—All enclosed in calyx.

*Hips.*—None.

*Sepals.*—Permanent; spear shaped; recurved.

*Seed.*—None.

Foliage:

*Leaves.*—Compound of seven leaflets; quite small; leathery; very glossy.

*Leaflets.*—Shape: broad lanceolate; nearly oval; apex acute; base rounded. Margin serrate. Color: medium green; new growth — normal (medium) green. Rachis: medium strength; upper side may have few tiny short hairs, grooved; underside — several short thorns. Stipules: medium long; medium width; short length; narrow points which turn out usually at about 45 degrees.

Growth:

*Habit.*—Much branched, spreading (rambler).

*Growth.*—Free vigorous; internodes short.

*Canes.*—Slender.

*Main stems.*—Color: medium green (bronzed on side exposed to sun).

*Thorns.*—Many; slender; hooked slightly downward; color — gray. Prickles/hairs — usually none.

*Branches.*—Color: Light to medium green. Thorns: numerous; medium length; slender; hooked slightly downward. Short oval base. Prickles/-hairs — usually none.

*Young shoots.*—Color: light to medium green. Thorns: numerous, slender; inclined slightly downward; color — reddish.

The climbing miniature rose plant and its flowers as herein described may vary in slight detail due to climatic, soil and cultural conditions under which the variety may be grown; the present description being of the variety as grown at Visalia, Calif. The following is claimed:

1. A new and distinct variety of climbing miniature rose plant of hardy, spreading, much branched habit (rambler type), substantially as illustrated and described, characterized by flowers which are of a general deep red color, the buds and flowers resembling Orange Triumph (polyantha — not patented) in general shape but of smaller size, with an abundance of small glossy foliage; and further characterized by (A) ease of propagation by cuttings or by budding; the suppleness of the canes which leads this variety to use as a ground cover or (by budding) as a weeping standard (tree), and (B) the abundance of flowers borne, usually in clusters.

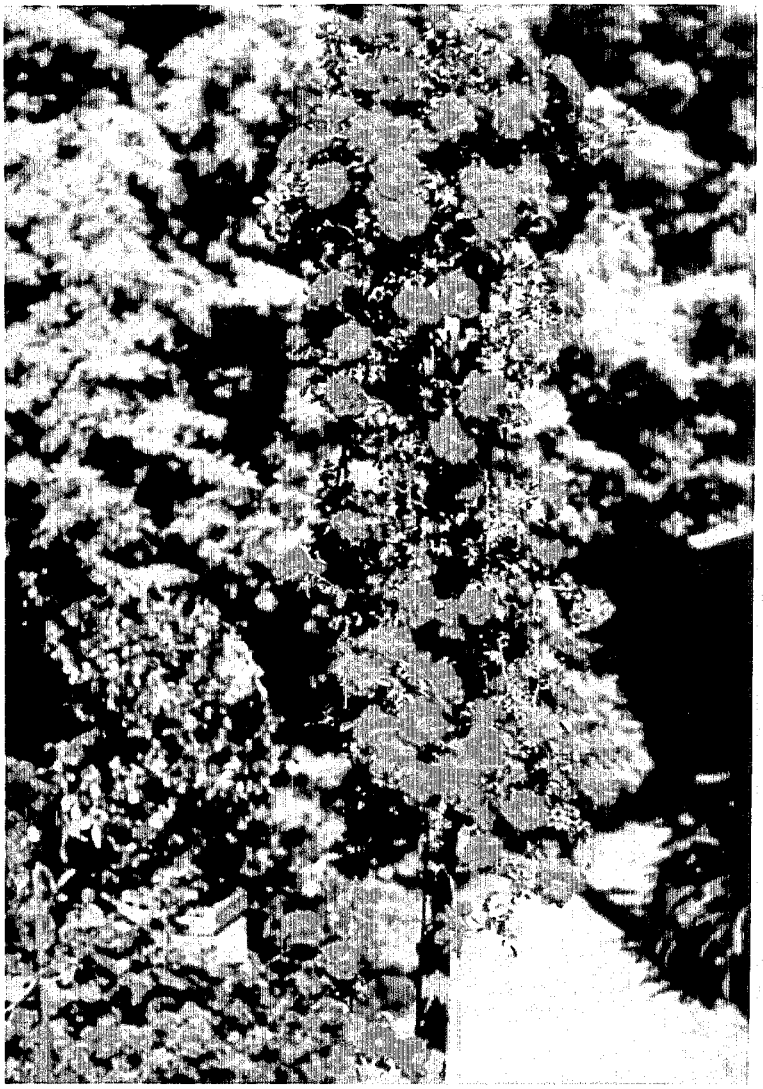

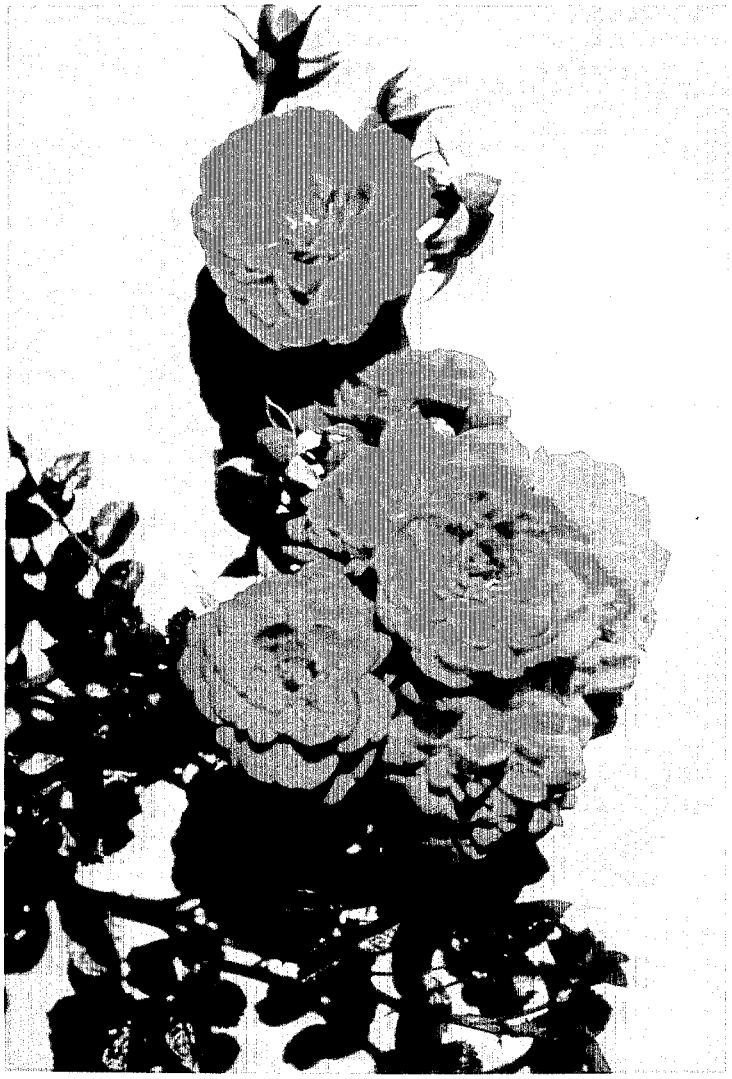

* * * * *